United States Patent
Vonderheiden (10) Patent No.: US 11,067,522 B2
(45) Date of Patent: Jul. 20, 2021

(54) MEASUREMENT SYSTEM FOR A CORRUGATING MACHINE

(71) Applicant: Texmag GmbH Vertriebsgesellschaft, Thalwil (CH)

(72) Inventor: Jörg Vonderheiden, Bargteheide (DE)

(73) Assignee: TEXMAG GMBH VERTRIEBSGESELLSCHAFT, Thalwil (CH)

( * ) Notice: Subject to any disclaimer, the term of this patent is extended or adjusted under 35 U.S.C. 154(b) by 375 days.

(21) Appl. No.: 16/160,376

(22) Filed: Oct. 15, 2018

(65) Prior Publication Data
US 2019/0120779 A1    Apr. 25, 2019

(30) Foreign Application Priority Data
Oct. 25, 2017   (DE) .......................... 102017219064.7

(51) Int. Cl.
G01N 25/72 (2006.01)
B31F 1/28 (2006.01)
G01N 33/34 (2006.01)
G01J 5/00 (2006.01)

(52) U.S. Cl.
CPC .......... *G01N 25/72* (2013.01); *B31F 1/2831* (2013.01); *G01J 5/00* (2013.01); *G01N 33/346* (2013.01); *G01J 2005/0077* (2013.01); *G01J 2005/0085* (2013.01)

(58) Field of Classification Search
CPC .... G01N 25/72; G01N 33/346; B31F 1/2831; G01J 5/00; G01J 2005/0077; G01J 2005/0085
See application file for complete search history.

(56) References Cited

U.S. PATENT DOCUMENTS

| | | | | | |
|---|---|---|---|---|---|
| 5,581,353 A | * | 12/1996 | Taylor | ................... | B31F 1/2831 250/559.23 |
| 5,663,565 A | * | 9/1997 | Taylor | ................... | G01N 21/35 250/339.11 |
| 5,676,790 A | * | 10/1997 | Burrows | ............... | B31F 1/2831 156/210 |

(Continued)

FOREIGN PATENT DOCUMENTS

JP         2004020243         1/2004

OTHER PUBLICATIONS

European Search Report for Application No. 18199522.6; dated Apr. 1, 2019, 9 pages.

(Continued)

*Primary Examiner* — Nathaniel T Woodward
*Assistant Examiner* — Philip L Cotey
(74) *Attorney, Agent, or Firm* — Shumaker, Loop & Kendrick, LLP (57) ABSTRACT

The present invention relates to a measurement system for use in a corrugating machine and a corrugating machine and a method of checking the process for producing paper adhesions with such a measurement system. The measurement system according to the invention for use in a corrugating machine comprises a measurement device. The measurement device can detect electromagnetic waves in the infrared range here and is aimed at a region of a transportation device of the corrugating machine in the direction of transportation downstream of an adhesion station of the corrugating machine.

15 Claims, 5 Drawing Sheets

(56) References Cited

U.S. PATENT DOCUMENTS

| | | | | |
|---|---|---|---|---|
| 6,470,294 B1* | 10/2002 | Taylor | ................... | B31F 1/2818 |
| | | | | 702/170 |
| 9,721,377 B2* | 8/2017 | Raunio | ................ | G01B 11/303 |
| 10,040,266 B2* | 8/2018 | Ohira | .................... | B31F 1/2818 |
| 2008/0317940 A1* | 12/2008 | Kohler | .................. | B31F 1/2818 |
| | | | | 427/8 |
| 2014/0347358 A1* | 11/2014 | Raunio | ..................... | G06T 7/42 |
| | | | | 345/421 |
| 2015/0104563 A1* | 4/2015 | Lowe | ........................ | C09J 5/06 |
| | | | | 427/8 |
| 2015/0158264 A1 | 6/2015 | Sofinowski | | |
| 2015/0360436 A1* | 12/2015 | Ohira | .................... | B31F 1/2818 |
| | | | | 156/250 |
| 2016/0009516 A1* | 1/2016 | Mark | ...................... | B41J 3/407 |
| | | | | 493/13 |

OTHER PUBLICATIONS

Johnson et al. "Corrugated board bonding defect visualization and characterization," published in International journal of Adhesion & Adhesives vol. 59 (2015) pp. 105-114, accepted Feb. 4, 2015 and available online Feb. 23, 2015.

* cited by examiner

MEASUREMENT SYSTEM FOR A CORRUGATING MACHINE

TECHNICAL FIELD

The present invention relates to a measurement system for use in a corrugating machine and a method of checking the process for producing paper adhesions.

BACKGROUND

When products are manufactured in the form of material webs including, in particular, paper adhesions such as corrugated cardboard adhesions, monitoring and/or automated quality assurance are of considerable importance in order to ensure sufficient adhesive quality. During the production of a corrugated cardboard web, for example of a one-sided corrugated cardboard web consisting of a corrugated paper web and a cover web, that is to say a flat paper web, an adhesive agent is applied to the corrugated paper web and/or the cover web. Immediately thereafter, the corrugated paper web and the cover web are put together and brought into contact so that the adhesive agent can produce an adhesive bond between the two webs at the contact points. Crucial to achieving a successful adhesive bond here are, amongst other things, the quantity and an even distribution of the adhesive agent applied. There are various monitoring systems which are used to check successful adhesion.

For example, the thickness of the adhesive film on an adhesive roller can be measured before and after the adhesive has been applied. It is then possible to determine indirectly whether a sufficient volume of adhesive could theoretically have been deposited at the point to be adhered. However, it is impossible to tell, using this system, whether this quantity of adhesive is also actually to be found at the point to be adhered, let alone whether the adhesive bonding of two webs has been brought about successfully.

Other approaches attempt to measure the thickness of the adhesive film after it has been applied to the corrugated paper web. Although the quantity of adhesive agent actually applied can be determined in this way, it is still impossible to tell whether there has been a successful adhesive bond after the adhesive has been applied and the two paper webs have been brought into contact.

The problem underlying the present invention is to provide a measurement system for judging the adhesive quality of paper adhesions, in particular for judging the adhesive quality of corrugated cardboard adhesions.

SUMMARY OF THE INVENTION

The present invention relates to a measurement system for use in a corrugating machine and a method of checking the process for producing paper adhesions.

In a first variation, the measurement system according to the invention for use in a corrugating machine comprises a measurement device. The measurement device can detect electromagnetic waves in the infrared range here and is aimed at a region of a transportation device of the corrugating machine in the direction of transportation downstream of an adhesion station of the corrugating machine.

Because the measurement device can detect infrared radiation, it is essentially possible to detect a temperature of corrugated cardboard. Based on the temperature, conclusions can be drawn regarding the quality of the corrugated cardboard, in particular regarding the quality of the corrugated cardboard adhesion. This is possible specifically because the measurement station is aimed at a region of the transportation device in the direction of transportation downstream of the adhesion station. In other words, this means that the corrugated cardboard can be checked after adhesion, that is to say after the adhesive agent has been applied and the two paper webs which are to be adhered have been brought into contact. This means that the adhesion of the corrugated cardboard is only checked when the adhesion process has been completed and the adhesive agent is in the process of hardening.

Generally speaking, a paper web is to be understood here to mean a continuous material made of paper. This may, for example, be a corrugated paper web or a flat paper web, also referred to as a cover web. One-sided corrugated cardboard is produced, for example, from one flat paper web and one corrugated paper web. Single-walled corrugated cardboard is produced, for example, from two flat paper webs and one corrugated paper web. It is also possible to distinguish between double-walled, triple-walled or multiple-walled corrugated cardboard, these essentially being defined by the number of corrugated paper webs they have. These can again be designed to be one-sided or single-walled respectively. For example, a double-walled corrugated cardboard is produced from three flat paper webs and two corrugated paper webs which are each located between two flat paper webs. The term corrugated cardboard can be understood in the context of this application both as the continuous product consisting of at least one flat paper web and one corrugated paper web, that is to say a corrugated cardboard web, and as a corrugated cardboard product, that is to say no longer in continuous form. The term product web generally refers, in the context of this application, to a product consisting of at least two webs or two paper webs.

Since, primarily through previous process steps, at least the corrugated paper web is in a heated state immediately before the adhesive is applied and the webs are brought into contact, the adhesive agent also heats up when the adhesive is applied to the respective paper web or at the latest when the two paper webs which are to be adhered are brought into contact. This means that, in the region of the adhesion, that is to say in the contact region of the paper webs which are to be adhered, there is a different temperature characteristic than in regions of the corrugated cardboard which are not adhered or are not in contact. In particular, the changing of the temperature at different points in the process differs considerably in the regions described above. Regions which are in contact and which have had adhesive agent applied to them cool slower here, for example, than regions which have neither had adhesive agent applied to them nor are in contact. It is therefore possible, on the basis of the temperature of the corrugated cardboard or on the basis of the heat radiated from a corrugated cardboard surface, to make a reliable judgment as to the quality of the corrugated cardboard adhesion. A corrugated cardboard surface may, for example, in the case of a one-sided corrugated cardboard, be intended to refer to both the surface of the cover web and the surface of the corrugated paper web.

In other words, this means that, during the adhesion process, the adhesive agent is heated in the adhesion station through contact with, in particular, the corrugated paper web and cools down together with the corrugated cardboard immediately thereafter. Depending on how much adhesive agent has been applied to an adhesion point between the paper webs which are to be adhered, the adhesive agent and therefore also the respective paper web or paper web surface also cools faster or slower in the region of the adhesion point. Similarly, the adhesive agent and also the respective paper web or paper web surface cools slower or faster depending on whether the paper webs which are to be adhered remain fully in contact or partially or completely separate after passing through the adhesion station. If, for example, too little adhesive agent has been applied or if the paper webs which are to be adhered have become separated from one another again after having been brought into contact, a lower temperature will be detected than with defect-free adhesion. Conversely, applying too much adhesive agent leads to a higher temperature being detected than with defect-free adhesion. The measurement system according to the invention therefore allows a reliable judgment to be made of the adhesion that actually exists, that is to say the state of the adhesion after the adhesion process. The check can also be carried out disruption-free and without affecting operational flow.

In configurations which can be combined with the preceding configuration, the measurement device may preferably comprise an imaging measurement device. This makes it possible, for example, to establish a thermographic evaluation of the measurement.

In configurations which can be combined with any of the preceding configurations, the measurement device can be configured to display a temperature distribution thermographically and to analyze it. Displaying the temperature distribution thermographically may, on the one hand, help an operator of the measurement device to understand the measurement result. For example, an operator can quickly give a qualitative assessment of the situation by looking at the thermographic display. On the other hand, a thermographic display may enable automated graphic evaluation of the measurement.

In configurations which can be combined with any of the preceding configurations, the measurement device can be configured to detect the temperature, preferably the surface temperature, of the corrugated cardboard. The measurement device can also be configured to judge a temperature distribution of the corrugated cardboard. Alternatively or in addition, the measurement device can be configured to detect a temperature distribution of the corrugated cardboard, preferably a temperature distribution of the corrugated cardboard along the width of the web. Since, in defect free adhesion, the temperature is normally distributed homogeneously or according to a specific pattern, in particular over the width of the web, the quality of the corrugated cardboard adhesion can be fully detected on the basis of the temperature distribution of the corrugated cardboard. This means that the measurement device can be configured to judge the adhesive quality of a corrugated cardboard adhesion, preferably on the basis of a temperature distribution of the corrugated cardboard.

In configurations which can be combined with any of the preceding configurations, the measurement device can be configured to judge a temperature distribution of the corrugated cardboard linearly and/or in matrix form. Alternatively or in addition, the measurement device may comprise an infrared camera.

In configurations which can be combined with any of the preceding configurations, the measurement device may also comprise an evaluation device for evaluating the detected electromagnetic waves in the infrared range. The evaluation device may comprise a computer with a memory device here. A computer program for checking the process of producing adhesions can be stored on the memory device. In particular, adhesions of a first paper web to at least a second paper web to form a product web can be checked here. The computer program can be configured to carry out the following steps here:

Detecting thermal radiation of the product web after adhesion of the first paper web to the at least second paper web,
Producing thermographic data based on the thermal radiation,
Evaluating the thermographic data, and
Judging the adhesive quality of the paper adhesion on the basis of the evaluation.

Through these particularly advantageous configurations, an automated quality check can be provided. The automated check also enables full monitoring of the adhesions. Automated identification of any defects at an early stage just downstream of the adhesion station means that the production process or the adhesion process can be quickly adjusted, meaning that the rejection of defective products can be massively reduced compared to quality control at a later point in the production process, for example when goods reach the output stage.

In configurations which can be combined with the preceding configuration, the detection may comprise detecting electromagnetic radiation in the infrared range. Alternatively or in addition, the thermal radiation of the product web in a detection region which extends linearly in the y direction of the product web and/or two-dimensionally in the x and y directions of the product web can be detected. Alternatively or in addition, the thermographic data may be produced in an evaluation region which is preferably a two-dimensional data region in the x and y directions. Alternatively or in addition, the adhesive quality can be judged on the basis of a geometric evaluation of the thermographic data. Through such advantageous configurations, it is possible to check not only whether the application of adhesive agent was sufficient or excessive, but also, irrespective of the application of the adhesive agent, whether successful adhesion has been achieved. This means that it can be checked whether the at least two paper webs which are to be adhered have also remained in contact after the adhesive agent has been applied and after they have been brought into contact. This is possible because the two paper webs which are to be adhered or else their surfaces have a specific temperature distribution and accordingly also specific thermographic properties on their surfaces, on the basis of which it is possible to determine the adhesion status.

In configurations which can be combined with either of the two preceding configurations, defects in the adhesion can be detected through geometric inhomogeneities in the thermographic data.

In configurations which can be combined with the preceding configuration, defects can be identified on the basis of geometric inhomogeneities which deviate from a prescribed pattern in the thermographic data. These geometric inhomogeneities include, in particular, circular geometric inhomogeneities, rectangular geometric inhomogeneities and/or geometric inhomogeneities essentially running over the entire width of the web in the y direction.

In configurations which can be combined with any of the four preceding configurations, the evaluation may comprise a spatially resolved determination of geometric dimensions of one or more isothermal regions and/or subregions in the thermographic data. The geometric dimensions of the one or more isothermal regions and/or subregions may preferably comprise the length in the x direction and/or the width in the y direction here.

In configurations which can be combined with the preceding configuration, the adhesive quality can be judged on the basis of a comparison of the geometric dimensions of the one or more isothermal regions and/or subregions of an adhesion with reference values of the geometric dimensions.

In configurations which can be combined with any of the six preceding configurations, the evaluation may comprise the formation of an integral over a linear subregion of the thermographic data of one or more isothermal regions and/or subregions in the x direction. The adhesive quality can be judged here on the basis of a comparison of the integral of the one or more isothermal regions and/or subregions of an adhesion with reference values of the respective integral.

In configurations which can be combined with any of the seven preceding configurations, the evaluation may comprise the formation of a surface integral over a subregion of the thermographic data of one or more isothermal regions and/or subregions in the x and y directions. The adhesive quality can be judged here on the basis of a comparison of the surface integral of the one or more isothermal regions and/or subregions of an adhesion with reference values of the respective surface integral.

In configurations which can be combined with any of the three preceding configurations, the reference values may comprise predetermined reference values. Alternatively or in addition, the reference values can be formed by taking an average of the previously checked adhesions. In particular, the reference values can be formed here by taking an average of the two previously checked adhesions, preferably of the five previously checked adhesions and particularly preferably of the at least ten previously checked adhesions.

In configurations which can be combined with any of the four preceding configurations, the adhesive quality can be judged as sufficient if the respective comparison shows a maximum deviation of 0% to 50%, preferably of 0% to 20% and particularly preferably of 0% to 5%.

In configurations which can be combined with any of the nine preceding configurations, detection of the thermal radiation can be carried out with an infrared camera.

In configurations which can be combined with any of the ten preceding configurations, the computer program can be configured to be implemented in-line during the process for producing paper adhesions, preferably corrugated cardboard adhesions.

The invention also comprises a corrugating machine. The corrugating machine comprises a transportation device for transporting corrugated cardboard in a direction of transportation. The corrugating machine also comprises an adhesion station which is configured to adhere a first paper web to at least a second paper web. The corrugating machine also comprises a measurement system for checking the process of producing adhesions of the corrugated cardboard. The measurement system may be a measurement system according to any of the preceding configurations here.

In configurations of the corrugating machine according to the invention which can be combined with the preceding configuration, the corrugating machine may also comprise heating elements which are arranged on the transportation device.

In configurations of the corrugating machine according to the invention which can be combined with either of the two preceding configurations, the corrugating machine may also comprise a rejection device. The rejection device can be arranged here in the direction of transportation downstream of the measurement system. The rejection device can also be configured to remove corrugated cardboard with an adhesive quality below a minimum level.

In configurations of the corrugating machine according to the invention which can be combined with any of the three preceding configurations, the measurement system can be aimed at a surface side of the first paper web, the normal vector thereof being aimed in the opposite direction of the second paper web. Alternatively or in addition, the measurement system can be aimed at a surface side of the at least second paper web, the normal vector thereof being aimed in the opposite direction of the first paper web. This means that the measurement device merely has to be aimed at one surface of a paper web and therefore also only needs to be arranged on one surface side of the paper web. Alternatively, however, the measurement device may also comprise two units which are arranged on both sides of the paper web in order to detect both surfaces of the paper web.

The invention also comprises a method of checking the process for producing adhesions of a first paper web to at least a second paper web to form a product web, using a measurement system. The method comprises the following steps here:

Detecting thermal radiation of the product web after adhesion of the first paper web to the at least second paper web, Producing thermographic data based on the thermal radiation, Evaluating the thermographic data, and Judging the adhesive quality of the paper adhesion on the basis of the evaluation.

Through these particularly advantageous configurations, an automated quality check can be provided. The automated check also enables full monitoring of the adhesions. Automated identification of any defects at an early stage just downstream of the adhesion station means that the production process or the adhesion process can be quickly adjusted, meaning that the rejection of defective products can be massively reduced compared to quality control at a later point in the production process, for example when goods reach the output stage.

In configurations of the method according to the invention which can be combined with the preceding configuration, the detection may comprise detecting electromagnetic radiation in the infrared range.

In configurations of the method according to the invention which can be combined with either of the two preceding configurations, the thermal radiation of the product web in a detection region can be detected. The detection region may extend linearly in the y direction of the product web here. Alternatively, the detection region may extend two-dimensionally in the x and y directions of the product web.

In configurations of the method according to the invention which can be combined with any of the three preceding configurations, the thermographic data may be produced in an evaluation region. The evaluation region may, in particular, be a two-dimensional data region in the x and y directions here.

In configurations of the method according to the invention which can be combined with any of the four preceding configurations, the adhesive quality can be judged on the basis of a geometric evaluation of the thermographic data. Through such advantageous configurations, it is possible to check not only whether the application of adhesive agent was sufficient or excessive, but also, irrespective of the application of the adhesive agent, whether successful adhesion has been achieved. This means that it can be checked whether the two paper webs which are to be adhered have also remained in contact after the adhesive agent has been applied and after they have been brought into contact. This is possible because the two paper webs which are to be adhered or their surfaces have a specific temperature distribution and accordingly also specific thermographic properties on their surfaces, on the basis of which it is possible to determine the adhesion status.

In configurations of the method according to the invention which can be combined with any of the five preceding configurations, defects in the adhesion can be detected through geometric inhomogeneities in the thermographic data.

In configurations of the method according to the invention which can be combined with the preceding configuration, defects can be identified on the basis of geometric inhomogeneities which deviate from a prescribed pattern in the thermographic data. These geometric inhomogeneities include, in particular, circular geometric inhomogeneities, rectangular geometric inhomogeneities and/or geometric inhomogeneities essentially running over the entire width of the web in the y direction.

In configurations of the method according to the invention which can be combined with any of the six preceding configurations, the evaluation may comprise a spatially resolved determination of geometric dimensions of one or more isothermal regions and/or subregions in the thermographic data. The geometric dimensions of the one or more isothermal regions and/or subregions may preferably comprise the length in the x direction and/or the width in the y direction here.

In configurations of the method according to the invention which can be combined with the preceding configuration, the adhesive quality can be judged on the basis of a comparison of the geometric dimensions of the one or more isothermal regions and/or subregions of an adhesion with reference values of the geometric dimensions.

In configurations of the method according to the invention which can be combined with any of the eight preceding configurations, the evaluation may comprise the formation of an integral over a linear subregion of the thermographic data of one or more isothermal regions and/or subregions in the x direction. The adhesive quality can additionally be judged here on the basis of a comparison of the integral of the one or more isothermal regions and/or subregions of an adhesion with reference values of the respective integral.

In configurations of the method according to the invention which can be combined with any of the nine preceding configurations, the evaluation may comprise the formation of a surface integral over a subregion of the thermographic data of one or more isothermal regions and/or subregions in the x and y directions. The adhesive quality can additionally be judged here on the basis of a comparison of the surface integral of the one or more isothermal regions and/or subregions of an adhesion with reference values of the respective surface integral.

In configurations of the method according to the invention which can be combined with any of the three preceding configurations, the reference values may comprise predetermined reference values. Alternatively or in addition, the reference values can be formed by taking an average of the previously checked adhesions. In particular, the reference values can be formed here by taking an average of the two previously checked adhesions, preferably of the five previously checked adhesions and particularly preferably of the at least ten previously checked adhesions.

In configurations of the method according to the invention which can be combined with any of the four preceding configurations, the adhesive quality can be judged as sufficient if the respective comparison shows a maximum deviation of 0% to 50%, preferably of 0% to 20% and particularly preferably of 0% to 5%.

In configurations of the method according to the invention which can be combined with any of the eleven preceding configurations, detection of the thermal radiation can be carried out with an infrared camera.

In configurations of the method according to the invention which can be combined with any of the twelve preceding configurations, the computer program can be configured to be implemented in-line during the process for producing paper adhesions, preferably corrugated cardboard adhesions.

In configurations of the method according to the invention which can be combined with any of the thirteen preceding configurations, the thermal radiation from one surface side of the first paper web can be detected, the normal vector thereof being aimed in the opposite direction of the second paper web. Alternatively or in addition, the thermal radiation from an at least second paper web can be detected, the normal vector thereof being aimed in the opposite direction of the first paper web.

In configurations of the method according to the invention which can be combined with any of the fourteen preceding configurations, the paper adhesion may, in particular, be a corrugated cardboard adhesion.

In configurations of the method according to the invention which can be combined with any of the fifteen preceding configurations, the paper web may, in particular, be a corrugated cardboard web.

In configurations of the method according to the invention which can be combined with any of the sixteen preceding configurations, the method can be carried out with a measurement system according to any of configurations 1 to 15.

DETAILED DESCRIPTION

Exemplary embodiments of the measurement system 1 according to the invention are described below by reference to the figures. In this application, the term width of the web 92a relates to an extent of a transportation device or of a product web/corrugated cardboard in the y direction 92 and the term direction of transportation 94a relates to a direction of conveyance of the transportation device or of the product web/corrugated cardboard in the x direction 94. The term paper web is to be understood here to refer to a continuous material made of paper. This may, for example, be a corrugated paper web or a flat paper web, also referred to as a cover web. One-sided corrugated cardboard is produced, for example, from one flat paper web and one corrugated paper web. Single-walled corrugated cardboard is produced, for example, from two flat paper webs and one corrugated paper web. It is also possible to distinguish between double-walled, triple-walled or multiple-walled corrugated cardboard, these essentially being defined by the number of corrugated paper webs they have. These can again be designed to be one-sided or single-walled respectively. For example, a double-walled corrugated cardboard is produced from three flat paper webs and two corrugated paper webs which are each located between two flat paper webs. The term corrugated cardboard can be understood in the context of this application both as the continuous product consisting of at least one flat paper web and one corrugated paper web, that is to say a corrugated cardboard web, and as a corrugated cardboard product, that is to say no longer in continuous form. The term product web generally refers, in the context of this application, to a product consisting of at least two webs or two paper webs.

Figure 1:
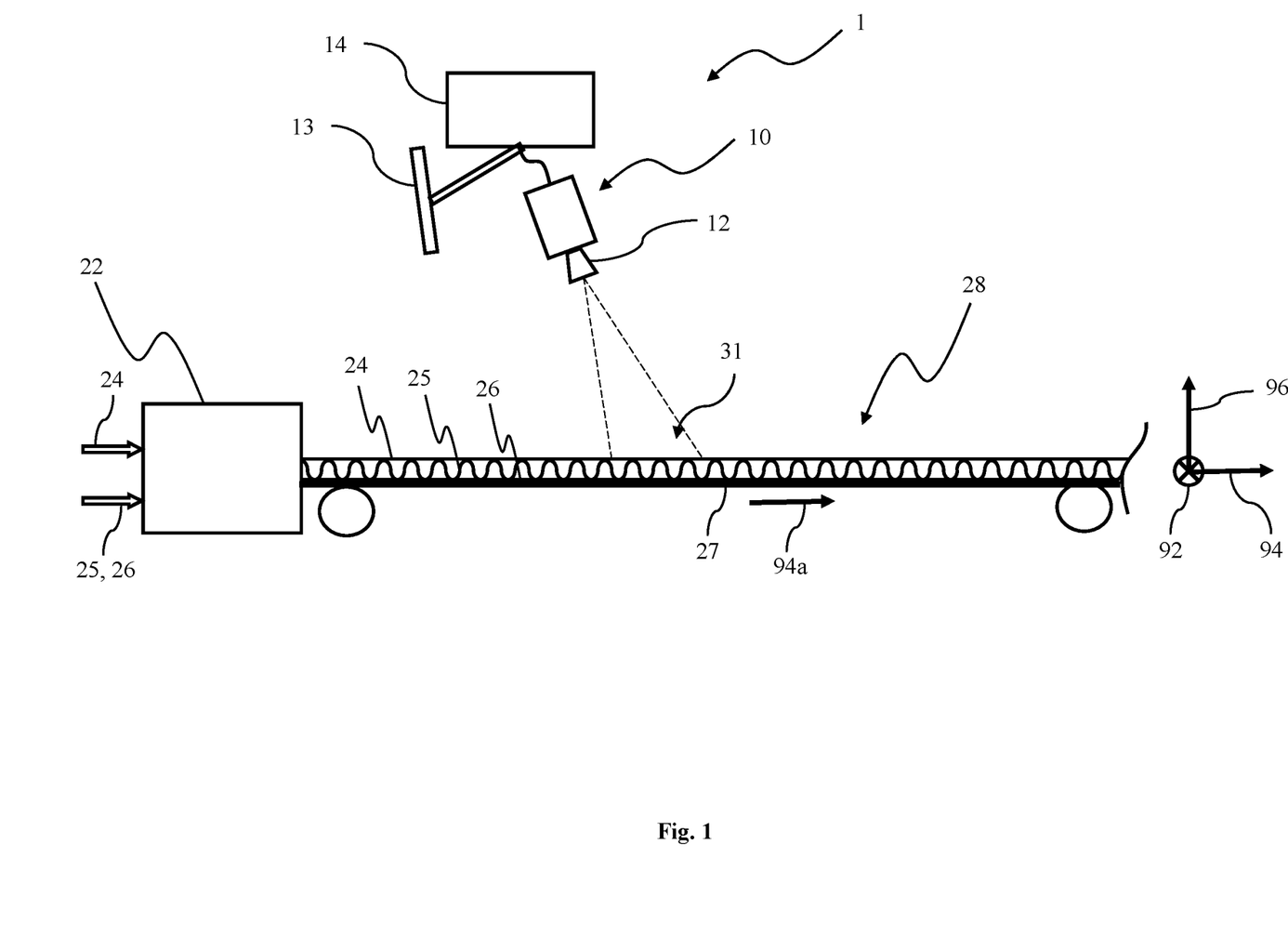
FIG. 1 shows a side view of the measurement system according to the invention with relative positioning in a corrugated cardboard machine

FIG. 1 shows an exemplary measurement system 1 for use in a corrugating machine. In a first variation, the measurement system 1 according to the invention for use in a corrugating machine comprises a measurement device 10. The measurement device 10 can detect electromagnetic waves in the infrared range here and is aimed at a region 31 of a transportation device 27 of the corrugating machine in the direction of transportation 94a downstream of an adhesion station 22 of the corrugating machine.

Because the measurement device 10 can detect infrared radiation, it is essentially possible to detect a temperature of the corrugated cardboard 28. Based on the temperature, conclusions can be drawn regarding the quality of the corrugated cardboard 28. This is possible specifically because the measurement station 1 is aimed at a region of the transportation device 27 in the direction of transportation 94a downstream of the adhesion station 22. In other words, this means that the corrugated cardboard 28 can be checked after adhesion, that is to say after the adhesive agent has been applied and the at least two paper webs (24, 25, 26) which are to be adhered have been brought into contact. This means that the adhesion of the corrugated cardboard is only checked when the adhesion process has virtually been completed and the adhesive agent is in the process of hardening. The gel point of the adhesive agent may lie within a temperature range of 40° C. to 70° C. here and preferably in a temperature range of 50° C. to 60° C. Particularly preferably, the gel point of the adhesive agent may lie at approx. 55° C.

Since, primarily through previous process steps, at least the corrugated paper web 25 is in a heated state immediately before the adhesive is applied and the webs are brought into contact, the adhesive agent also heats up when the adhesive is applied to the respective paper web (24, 25, 26) or at the latest when the two paper webs (24, 25, 26) which are to be adhered are brought into contact. This means that, in the region of the adhesion, that is to say in the contact region of the paper webs (24, 25, 26) which are to be adhered, there is a different temperature characteristic than in regions of the corrugated cardboard 28 which are not adhered or are not in contact. In particular, the changing of the temperature at different points in the process differs considerably in the regions described above. Regions which are in contact and which have had adhesive agent applied to them cool slower here, for example, than regions which have neither had adhesive agent applied to them nor are in contact. The temperatures on the surface of the corrugated cardboard or on the at least two paper webs may lie between 30° C. and 130° C., in particular between 60° C. and 120° C., here depending on the processing location. It is therefore possible, on the basis of the temperature of the corrugated cardboard 28 or on the basis of the heat radiated from a corrugated cardboard surface, to make a reliable judgment as to the quality of the corrugated cardboard adhesion. A corrugated cardboard surface may, for example, in the case of a one-sided corrugated cardboard, be intended to refer to both the surface of the cover web (24, 26) and the surface of the corrugated paper web (25).

In other words, this means that, during the adhesion process, the adhesive agent is heated in the adhesion station 22 through contact with, in particular, the corrugated paper web 25 and cools down together with the corrugated cardboard 28 immediately thereafter. Depending on how much adhesive agent has been applied to an adhesion point between the paper webs (24, 25, 26) which are to be adhered, the adhesive agent and therefore also the respective paper web (24, 25, 26) or paper web surface also cools faster or slower in the region of the adhesion point. Similarly, the adhesive agent and also the respective paper web (24, 25, 26) or paper web surface cools slower or faster depending on whether the paper webs which are to be adhered remain fully in contact or partially or completely separate after passing through the adhesion station 22. If, for example, too little adhesive agent has been applied or if the paper webs (24, 25, 26) which are to be adhered have become separated from one another again after having been brought into contact, a lower temperature will be detected than with defect-free adhesion. Conversely, applying too much adhesive agent leads to a higher temperature being detected than with defect-free adhesion. The measurement system 1 according to the invention therefore allows a reliable judgment to be made of the adhesion that actually exists, that is to say the state of the adhesion after the adhesion process. The check can also be carried out disruption-free and without affecting operational flow.

FIG. 1 also shows a coordinate system (92, 94, 96). The x direction 94 is understood here to be a direction in which the corrugated cardboard is conveyed. The y direction 92 designates a direction which is orthogonal to the x direction 94 within the plane of the web. The z direction is to be understood to be a direction which extends in a normal direction from the plane of the web, that is to say orthogonally to the x direction 94 and orthogonally to the y direction 92.

Figures 2A, 2B, 2C:
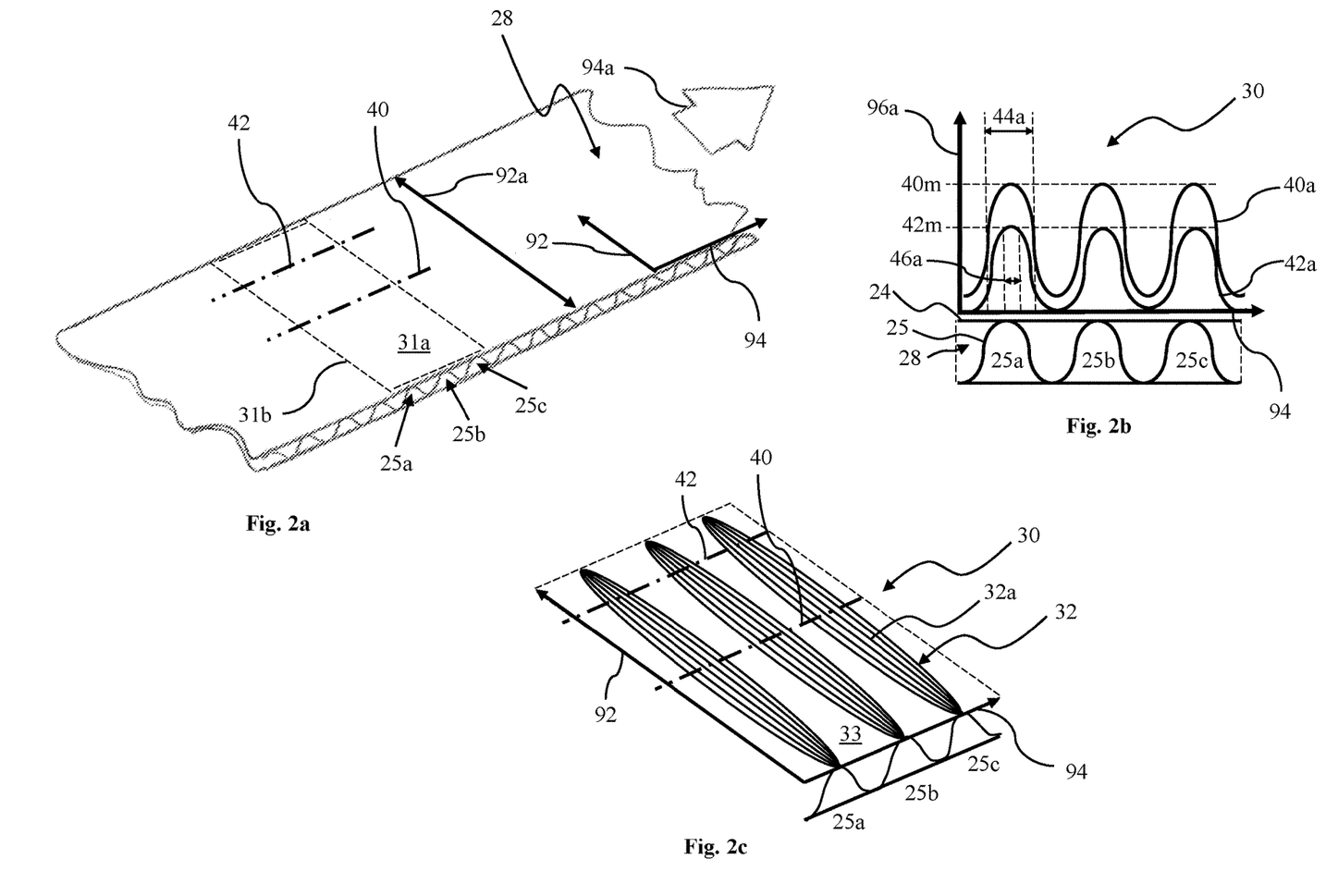
FIGS. 2a-c show an isometric view of the material web, an associated thermographic view and a temperature distribution diagram of a defect-free adhesion

FIG. 2a shows a detail of the transportation device 27 or of the corrugated cardboard web 28 with a detection region (31, 31a, 31b) of the measurement system 1 or of the measurement device 10. As can be seen here in particular, the measurement device 10 can be configured to judge a temperature distribution of the corrugated cardboard 28 linearly 31b, for example along the dotted detection line 31b which runs in the y direction 92. Alternatively or in addition, the measurement device 10 can be configured to judge a temperature distribution of the corrugated cardboard 28 in matrix form 31a, for example on the basis of the detection region 31a which extends in the x direction 94 and in the y direction 92. Alternatively or in addition, the measurement device 10 may comprise an infrared camera 12 (see FIG. 1).

The measurement device 10 may preferably also comprise an imaging measurement device 13 (see FIG. 1). This makes it possible, for example, to establish a thermographic evaluation of the measurement. The measurement device 10 can also be configured to display a temperature distribution (40a, 42a, 340a, 342a) thermographically and analyze it (see, in particular, FIGS. 2b-c and FIGS. 3b-c). Displaying the temperature distribution (40a, 42a, 340a, 342a) thermographically may, on the one hand, help an operator of the measurement device 10 to understand the measurement result. For example, an operator can quickly give a qualitative assessment of the situation by looking at the thermographic display. On the other hand, a thermographic display may enable automated graphic evaluation of the measurement.

In configurations which can be combined with any of the preceding configurations, the measurement device 10 can be configured to detect the temperature, preferably the surface temperature, of the corrugated cardboard 28. The measurement device 10 can also be configured to judge a temperature distribution (40a, 42a, 340a, 342a) of the corrugated cardboard 28. Alternatively or in addition, the measurement device 10 can be configured to detect a temperature distribution (40a, 42a, 340a, 342a) of the corrugated cardboard 28, preferably a temperature distribution of the corrugated cardboard along the width of the web 92a. Since, in defect free adhesion, the temperature is normally distributed homogeneously or according to a specific pattern 32 (see FIG. 2c which is explained in detail later), in particular over the width of the web 92a, the quality of the corrugated cardboard adhesion can be fully detected on the basis of the temperature distribution (40a, 42a, 340a, 342a) of the corrugated cardboard 28. This means that the measurement device 10 can be configured to judge the adhesive quality of a corrugated cardboard adhesion, preferably on the basis of a temperature distribution (40a, 42a, 340a, 342a) of the corrugated cardboard 28.

As can be seen in FIG. 1, the measurement device 10 may also comprise an evaluation device 14 for evaluating the detected electromagnetic waves in the infrared range. The evaluation device 14 may comprise a computer with a memory device here. A computer program for checking the process of producing adhesions can be stored on the memory device. In particular, adhesions of a first paper web 24 to at least a second paper web (25, 26) to form a product web (28) can be checked here. The computer program can be configured to carry out the following steps here:
  Detecting thermal radiation of the product web 28 after adhesion of the first paper web 24 to the at least second paper web (25, 26),
  Producing thermographic data 30 on the basis of the thermal radiation (see FIG. 2c and FIG. 3c),
  Evaluating the thermographic data 30 (see FIG. 3-FIG. 5), and
  Judging the adhesive quality of the paper adhesion on the basis of the evaluation.

Through these particularly advantageous configurations, an automated quality check can be provided. The automated check also enables full monitoring of the adhesions. Automated identification of any defects at an early stage just downstream of the adhesion station 22 means that the production process or the adhesion process can be quickly adjusted, meaning that the rejection of defective products can be massively reduced compared to quality control at a later point in the production process, for example when goods reach the output stage.

In configurations which can be combined with the preceding configuration, the detection may comprise detecting electromagnetic radiation in the infrared range. Alternatively or in addition, the thermal radiation of the product web 28 can be detected in a detection region 31 which extends linearly 31b in the y direction of the product web 28. Alternatively or in addition, the thermal radiation of the product web 28 can be detected in a detection region 31 which extends two-dimensionally 31a in the x and y directions of the product web 28. Alternatively or in addition, the thermographic data 30 may be produced in an evaluation region 33 which is preferably a two-dimensional data region in the x direction 94 and y direction 92. Alternatively or in addition, the adhesive quality can be judged on the basis of a geometric evaluation of the thermographic data 30.

In relation hereto, FIG. 2b shows the temperature distributions of a defect-free corrugated cardboard 28 along a first exemplary measurement region 40 and a second exemplary measurement region 42 within the detection region 31a from FIG. 2a. The curves of the temperature distributions of the measurement regions (40, 42) in FIG. 2b show here the change of temperature 96a of the corrugated cardboard surface in the x direction 94 within the detection region 31a in each case over three corrugations (25a, 25b, 25c) of the corrugated cardboard 28 at an exemplary position on the y axis 92 respectively. As already mentioned above, it can be seen from FIG. 2b that the temperature on the surface of the corrugated cardboard 28, that is to say, in the exemplary embodiment shown, the surface temperature of the flat paper web 24, is highest in the region of contact with the at least second paper web 25, in this case the corrugated paper web 25. The maximum temperatures in the respective measurement regions (40, 42) are indicated by the dotted lines 40m and 42m. It can also be seen from the exemplary temperature distribution (40a, 42a) in FIG. 2b that, when viewed in the direction of the edge region, that is to say in the direction of transportation 94a, the corrugated cardboard 28 has lower temperatures on the right and left at the edge of the width of the web 92a than in the middle of the web (see FIG. 2c). This is particularly clear from FIG. 2c which shows an evaluation region 33 corresponding to the detection region 31a and having exemplary isotherms 32a. It can be seen that the thermographic data 30 of the defect-free corrugated cardboard adhesion have a characteristic pattern 32. For example, the extent of the isotherms at the temperature 42m in the x direction 94 for the measurement region 40 corresponds to the characteristic distance 44a and for the measurement region 42 to the characteristic distance 46a (in each case measured in the region of the corrugation 25a).

Figures 3A, 3B, 3C:
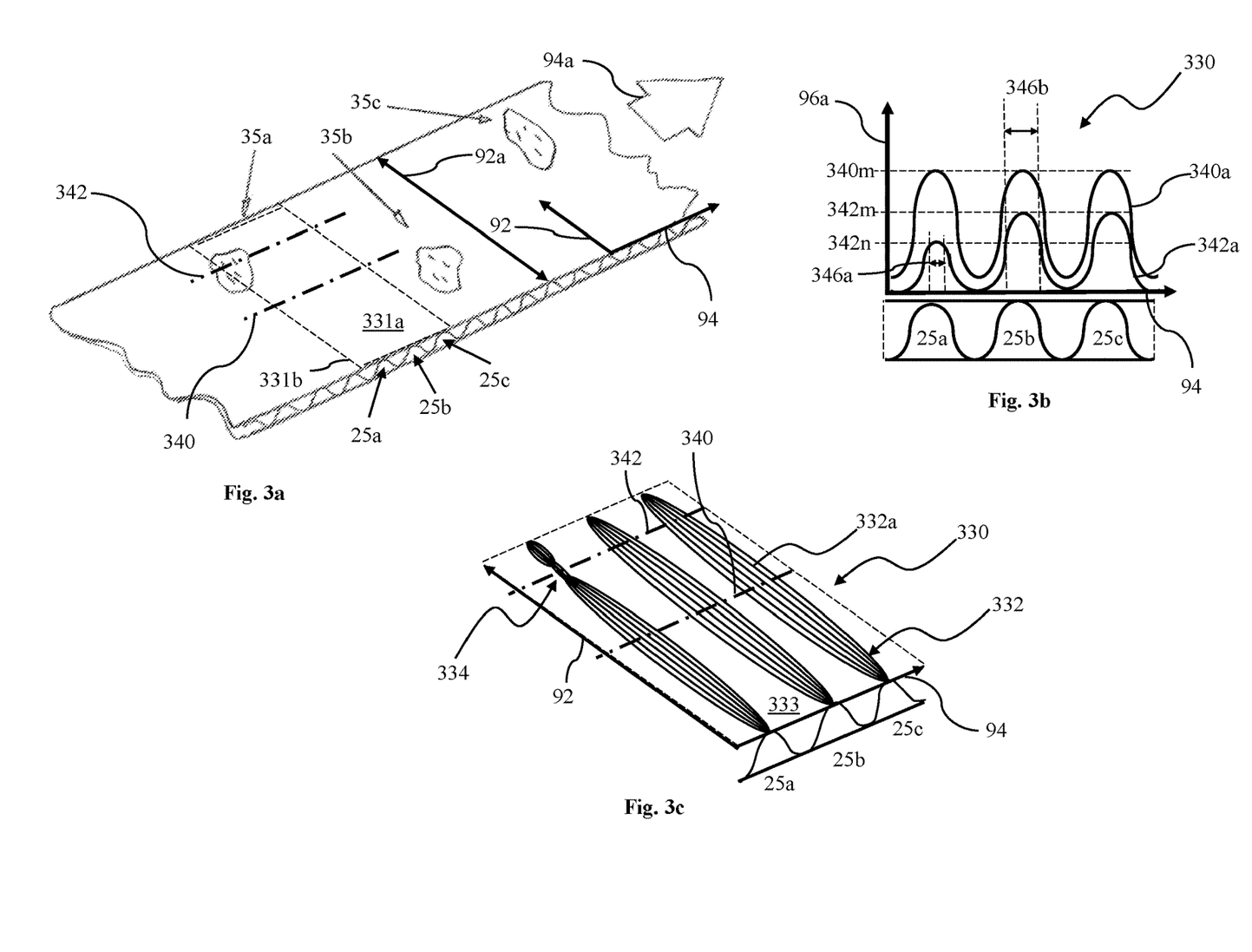
FIGS. 3a-c show an isometric view of the material web, an associated thermographic view and a temperature distribution diagram of a defective adhesion with geometric evaluation

Compared to the above, FIG. 3a-FIG. 3c show a defective corrugated cardboard adhesion with corresponding thermographic data 330. As an example, three surface defects (35a, 35b, 35c) are shown in FIG. 3a. However, in alternative embodiments, other types of defects, in particular defects in the edge region of the product web 28 and/or defects over the entire width of the web 92a, can also be detected. As in FIG. 2a-FIG. 2c, two exemplary measurement regions (340, 342) and temperature distributions (340a, 342a) are again shown in FIG. 3a-FIG. 3c. The defect 35a overlaps measurement region 342 and, more specifically, the first corrugation 25a therein and can be seen at the lower maximum temperature 342n in FIG. 3b. In the thermographic data 330 of FIG. 3c, the defect 35a can be seen as geometric inhomogeneity 334. Since the maximum temperature 342n at the location of the defect 35a is lower than at a defect-free point (cf. for example 342m for corrugation 25b in FIG. 3b or 42m for corrugation 25a in FIG. 2b), a defect 35 has to be assumed as a result of the paper webs which are to be adhered (24, 25, 26) becoming separated and/or too little adhesive agent being applied in the adhesion station 22. If the defect 35c had been caused by too much adhesive agent being applied, this would result in maximum 342n being greater than maximum 342m for defect-free adhesion and/or in distance 346a being greater than distance 346b for defect-free adhesion (see FIG. 3a and FIG. 3b). Similarly, in the latter case, the inhomogeneity 334 would extend further in the x direction 94 than the isotherms 332a in the region of the corrugations 25b and 25c in another position of the measurement region 342 in the x direction 94.

Through such advantageous configurations, it is possible to check not only whether the application of adhesive agent was sufficient or excessive, but also, irrespective of the application of the adhesive agent, whether successful adhesion has been achieved. This means that it can be checked whether the paper webs (24, 25, 26) which are to be adhered have also remained in contact after the adhesive agent has been applied and after they have been brought into contact. This is possible because the paper webs (24, 25, 26) which are to be adhered or else their surfaces have a specific temperature distribution (40a, 42a, 340a, 342a) and accordingly also specific thermographic properties on their surfaces, on the basis of which it is possible to determine the adhesion status.

This means that defects 35 in the adhesion can be detected through geometric inhomogeneities 334 in the thermographic data (30, 330). Defects 35 can also be identified on the basis of geometric inhomogeneities 334 which deviate from a prescribed pattern (32, 332) in the thermographic data (30, 330). The defects can also be detected on the basis of a deviation in temperature from a defect-free adhesion. A deviation in temperature of more than 3° C., in particular of more than 5° C., for example, can serve as an indicator of an anomaly or defect. The respective defect or an event can be classified on the basis of a combination of the deviation in temperature and the geometric shape. These geometric inhomogeneities 334 include, in particular, circular geometric inhomogeneities, rectangular geometric inhomogeneities and/or geometric inhomogeneities essentially running over the entire width of the web 92a in the y direction 92. In other words, this means that thermographic data (30, 330, 430, 530) on the basis of which the evaluation and judgment are carried out can be produced on the basis of detected thermal radiation.

As already mentioned in connection with FIG. 3b, the evaluation may comprise a spatially resolved determination of geometric dimensions of one or more isothermal regions (32a, 332a) and/or subregions in the thermographic data (30, 330). The geometric dimensions of the one or more isothermal regions (32a, 332a) and/or subregions may preferably comprise the length in the x direction 94 and/or the width in the y direction 92. As an example, an evaluation of the length of the isothermal subregions in the x direction 94 has already been explained in connection with FIG. 2b and FIG. 3b. The adhesive quality can be judged here on the basis of a comparison of the geometric dimensions of the one or more isothermal regions (32a, 332a) and/or subregions of an adhesion with reference values of the geometric dimensions. In the exemplary embodiment in FIG. 3b, for example, it could be checked whether the adhesion is defect-free by comparing the length 346a with the length 346b of a defect-free adhesion at a corresponding position in the y direction 92 of an isotherm. Both a predetermined reference value and a reference value formed by taking an average of the previously checked adhesions may serve as the reference value here. In particular, the reference values can be formed here by taking an average of the two previously checked adhesions, preferably of the five previously checked adhesions and particularly preferably of the at least ten previously checked adhesions. Alternatively, the reference value can also be manually input or amended by a machine operator. An adhesion can be judged as defect-free or the adhesive quality can be judged as sufficient here if the respective comparison shows a maximum deviation of 0% to 50%, preferably of 0% to 20% and particularly preferably of 0% to 5%.

Figure 4:
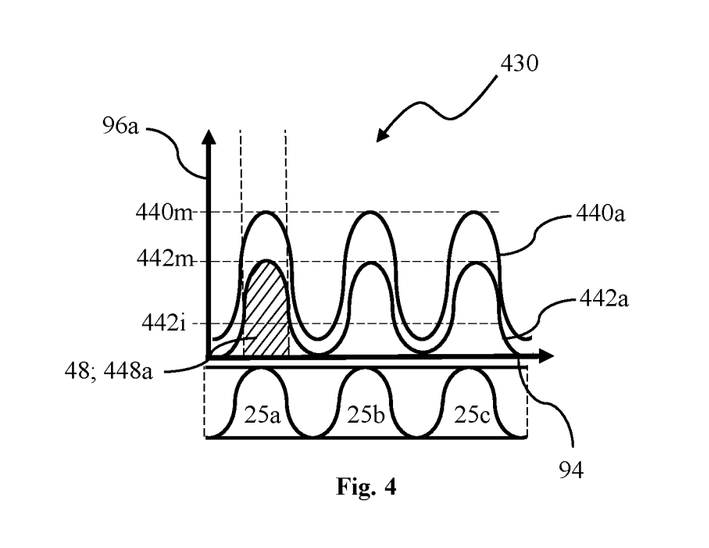
FIG. 4 shows a temperature distribution diagram with thermographic data of a defect-free material web as from FIGS. 2a-c with integral evaluation
Figure 5:
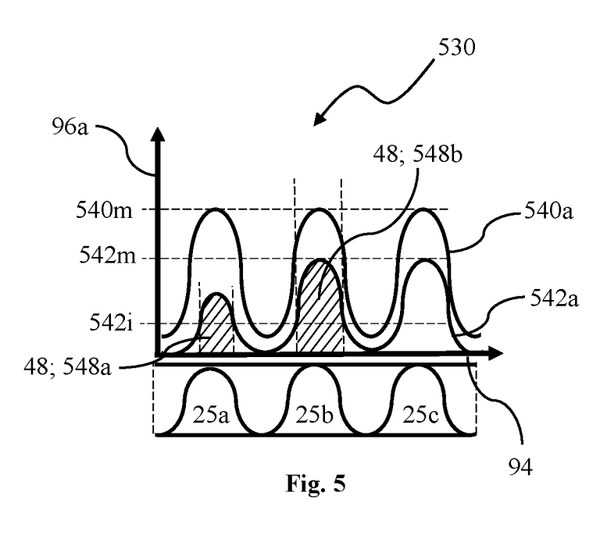
FIG. 5 shows a temperature distribution diagram with thermographic data of a defective material web as from FIGS. 3a-c with integral evaluation

Alternatively or in addition, the evaluation may comprise the formation of an integral 48 over a linear subregion of the thermographic data (30, 330, 430, 530) of one or more isothermal regions (32a, 332a) and/or subregions in the x direction 94. The adhesive quality can be judged here on the basis of a comparison of the integral 48 of the one or more isothermal regions (32a, 332a) and/or subregions of an adhesion with reference values of the respective integral 48. In relation hereto, FIG. 4 and FIG. 5 respectively show a thermographic representation corresponding to FIG. 2b and FIG. 3b, but with integral evaluation. The temperature distributions (440a, 442a) for the two measurement regions (40, 42) of a defect-free adhesion from FIG. 2a can again be seen in FIG. 4. As an example, FIG. 4 shows, in the region of the corrugation 25a, an integral 448a for a comparative temperature 442i, which serves to delimit the integration region. FIG. 5, on the other hand, shows the temperature distributions (540a, 542a) for the two measurement regions (340, 342) of a defective adhesion from FIG. 3a. As in FIG. 4, a comparative temperature 542i which serves to delimit the integration region is indicated in FIG. 5. As a result of the defect 35a (see FIG. 3a) in the region of the corrugation 25a of the measurement region 342, the temperature 96a and therefore also the integral 548a in the region of the corrugation 25a of the measurement region 342 is significantly smaller than an integral in a defect-free region (see integrals 448a and 548b).

Alternatively or in addition, the evaluation may comprise the formation of a surface integral over a subregion of the thermographic data (30, 330, 430, 530) of one or more isothermal regions (32a, 332a) and/or subregions in the x direction 94 and the y direction 92. The adhesive quality can be judged here on the basis of a comparison of the surface integral of the one or more isothermal regions (32a, 332a) and/or subregions of an adhesion with reference values of the respective surface integral. The reference values for the comparison with the integral in the x direction 94 and/or the surface integral in the x direction 94 and the y direction 92 may comprise predetermined reference values here. Alternatively or in addition, the reference values can also be formed by taking an average of the previously checked adhesions. In particular, the reference values can be formed here by taking an average of the two previously checked adhesions, preferably of the five previously checked adhesions and particularly preferably of the at least ten previously checked adhesions. Alternatively, the reference value can also be manually input or amended by a machine operator. An adhesion can be judged as defect-free or the adhesive quality can be judged as sufficient here if the respective comparison shows a maximum deviation of 0% to 50%, preferably of 0% to 20% and particularly preferably of 0% to 5%.

Alternatively or in addition, the evaluation may also comprise a comparison of the thermographic data (30, 330, 430, 530) with a thermographic golden template. The thermographic golden template represents here the thermographic template corresponding to a perfect adhesion or the thermographic data corresponding to a perfect adhesion.

The detection of the thermal radiation can also be carried out with an infrared camera 12 (see FIG. 1).

The computer program can also be configured to be implemented in-line during the process for producing paper adhesions, preferably corrugated cardboard adhesions.

Figure 6:
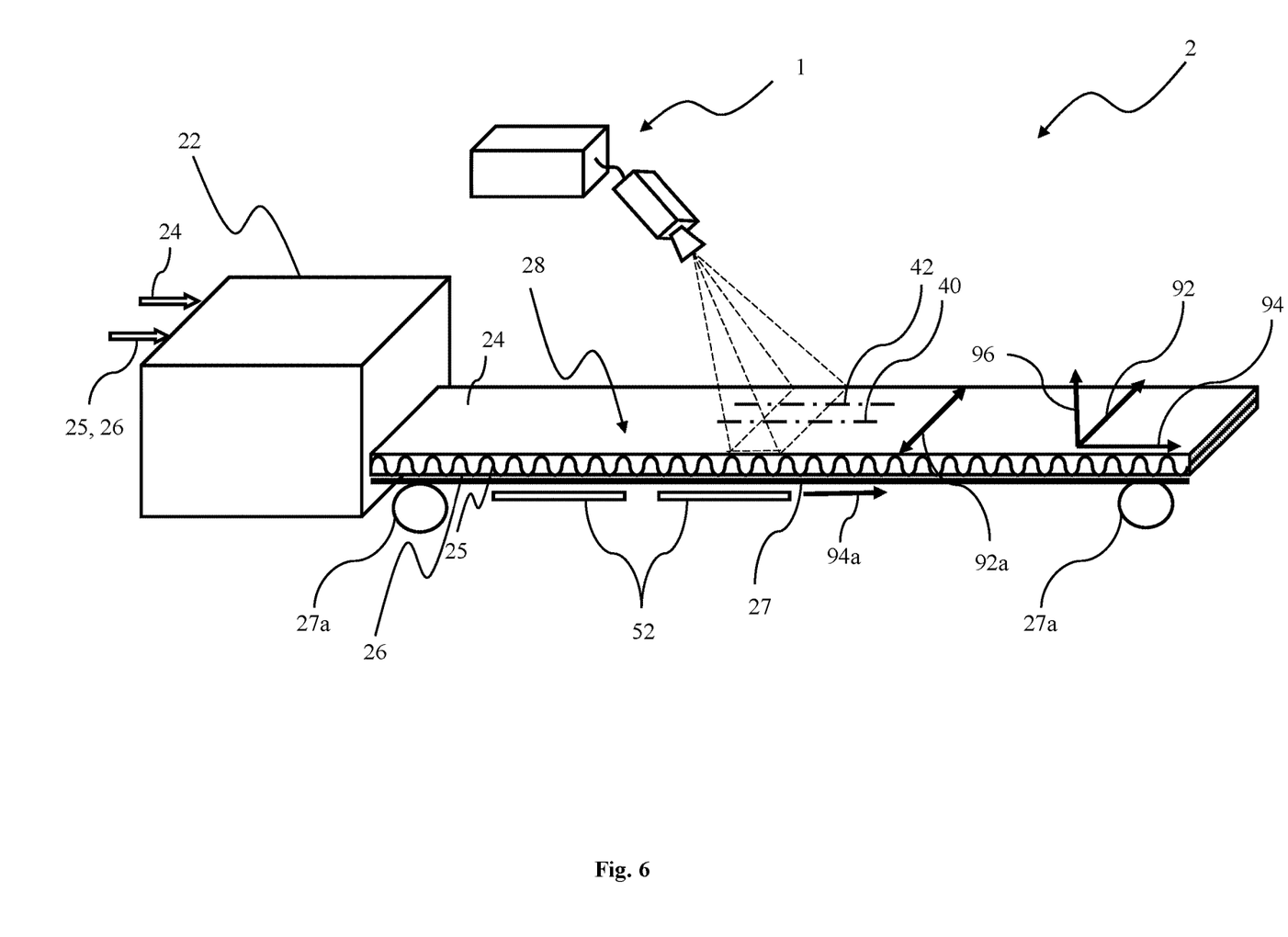
FIG. 6 shows an isometric view of the corrugating machine according to the invention with measurement system and adhesion station

As shown in FIG. 6, the invention also comprises a corrugating machine 2. The corrugating machine 2 comprises a transportation device 27 for transporting corrugated cardboard 28 in a direction of transportation 94a. The transportation device 27 may comprise a conveyor belt with rollers 27a or simply just conveying rollers 27a here. The corrugating machine 2 also comprises an adhesion station 22 which is configured to adhere a first paper web 24 to at least a second paper web (25, 26). The corrugating machine 2 also comprises a measurement system for checking the process of producing the corrugated cardboard 28. The measurement system may be a measurement system 1 according to any of the preceding configurations here.

The corrugating machine 2 may also comprise heating elements 52 which are arranged on the transportation device 27. Alternatively and in particular if the transportation device 27 only comprises conveying rollers 27a, the heating elements 52 may also be arranged directly on the corrugated cardboard 28, for example in the negative z direction 96 with a gap under the corrugated cardboard 28. Alternatively, the heating elements 52 may also be arranged in another position in the x direction 94 and/or on the other side of the corrugated cardboard web 28 in the positive z direction 96.

The corrugating machine 2 may also comprise a rejection device which is not shown here. The rejection device can be arranged here in the direction of transportation 94a downstream of the measurement system 1 here. The rejection device can also be configured to remove corrugated cardboard with an adhesive quality below a minimum level.

In configurations of the corrugating machine 2 according to the invention which can be combined with any of the three preceding configurations, the measurement system 1 can be aimed at a surface side of the first paper web 24, the normal vector thereof being aimed in the opposite direction of the at least second paper web (25, 26). Alternatively or in addition, the measurement system 1 can be aimed at a surface side of the at least second paper web (25, 26), the normal vector thereof being aimed in the opposite direction of the first paper web 24. This means that the measurement device 1 merely has to be aimed at one surface of a product web 28 and therefore also only needs to be arranged on one surface side of the product web 28. Alternatively, however, the measurement device 1 may also comprise two units which are arranged on both sides of the product web 28 in order to detect both surfaces of the product web 28. In the example in FIG. 6, an upper, flat paper web 24 and a lower, flat paper web 26 are being adhered to a corrugated paper web 25 arranged in between them. Since the transportation device 27, as already mentioned, may also only comprise conveying rollers 27a, the adhesion of the lower, flat paper web 26 to the corrugated paper web 25 could also be checked by a measurement system 1 with a second measurement device (not shown) which is aimed at the surface of the lower paper web 26. Alternatively, the measurement system 1 can also be aimed only at the surface of the lower paper web 26 in order to check the adhesion of the lower, flat paper web 26 to the corrugated paper web 25. Alternatively, in particular in embodiments for the production of a one-sided corrugated cardboard 28, the measurement system 1 can also be aimed at the surface of the corrugated paper web 25.

The invention also comprises a method of checking the process for producing adhesions of a first paper web 24 to at least a second paper web (25, 26) to form a product web (28), using a measurement system. The method comprises the following steps here:

Detecting thermal radiation of the product web 28 after adhesion of the first paper web 24 to the at least second paper web (25, 26),
Producing thermographic data (30, 330) on the basis of the thermal radiation (see FIG. 2c and FIG. 3c),
Evaluating the thermographic data (30, 330, 430, 530) (see FIG. 3-FIG. 5), and
Judging the adhesive quality of the paper adhesion on the basis of the evaluation.

Through these particularly advantageous configurations, an automated quality check can be provided. The automated check also enables full monitoring of the adhesions. Automated identification of any defects at an early stage just downstream of the adhesion station 22 means that the production process or the adhesion process can be quickly adjusted, meaning that the rejection of defective products can be massively reduced compared to quality control at a later point in the production process, for example when goods reach the output stage.

In configurations which can be combined with the preceding configuration, the detection may comprise detecting electromagnetic radiation in the infrared range. Alternatively or in addition, the thermal radiation of the product web 28 can be detected in a detection region 31 which extends linearly 31b in the y direction of the product web 28. Alternatively or in addition, the thermal radiation of the product web 28 can be detected in a detection region 31 which extends two-dimensionally 31a in the x and y directions of the product web 28. Alternatively or in addition, the thermographic data 30 may be produced in an evaluation region which is preferably a two-dimensional data region in the x direction 94 and y direction 92. Alternatively or in addition, the adhesive quality can be judged on the basis of a geometric evaluation of the thermographic data 30.

Through such advantageous configurations, it is possible to check not only whether the application of adhesive agent was sufficient or excessive, but also, irrespective of the application of the adhesive agent, whether successful adhesion has been achieved. This means that it can be checked whether the paper webs (24, 25, 26) which are to be adhered have also remained in contact after the adhesive agent has been applied and after they have been brought into contact. This is possible because the paper webs (24, 25, 26) which are to be adhered or else their surfaces have a specific temperature distribution (40a, 42a, 340a, 342a) and accordingly also specific thermographic properties on their surfaces, on the basis of which it is possible to determine the adhesion status.

This means that defects 35 in the adhesion can be detected through geometric inhomogeneities 334 in the thermographic data (30, 330). Defects 35 can also be identified on the basis of geometric inhomogeneities 334 which deviate from a prescribed pattern (32, 332) in the thermographic data (30, 330). These geometric inhomogeneities 334 include, in particular, circular geometric inhomogeneities, rectangular geometric inhomogeneities and/or geometric inhomogeneities essentially running over the entire width of the web 92a in the y direction 92. In other words, this means that thermographic data (30, 330, 430, 530) on the basis of which the evaluation and judgment are carried out can be produced on the basis of detected thermal radiation.

As already mentioned in connection with FIG. 3b, the evaluation may comprise a spatially resolved determination of geometric dimensions of one or more isothermal regions (32a, 332a) and/or subregions in the thermographic data (30, 330). The geometric dimensions of the one or more isothermal regions (32a, 332a) and/or subregions may preferably comprise the length in the x direction 94 and/or the width in the y direction 92 here. As an example, an evaluation of the length of the isothermal subregions in the x direction 94 has already been explained in connection with FIG. 2b and FIG. 3b. The adhesive quality can be judged here on the basis of a comparison of the geometric dimensions of the one or more isothermal regions (32a, 332a) and/or subregions of an adhesion with reference values of the geometric dimensions. In the exemplary embodiment in FIG. 3b, for example, it could be checked whether the adhesion is defect-free by comparing the length 346a with the length 346b of a defect-free adhesion at a corresponding position in the y direction 92 of an isotherm. Both a predetermined reference value and a reference value formed by taking an average of the previously checked adhesions may serve as the reference value here. In particular, the reference values can be formed here by taking an average of the two previously checked adhesions, preferably of the five previously checked adhesions and particularly preferably of the at least ten previously checked adhesions. Alternatively, the reference value can also be manually input or amended by a machine operator. An adhesion can be judged as defect-free or the adhesive quality can be judged as sufficient here if the respective comparison shows a maximum deviation of 0% to 50%, preferably of 0% to 20% and particularly preferably of 0% to 5%.

Alternatively or in addition, the evaluation may comprise the formation of an integral 48 over a linear subregion of the thermographic data (30, 330, 430, 530) of one or more isothermal regions (32a, 332a) and/or subregions in the x direction 94. The adhesive quality can be judged here on the basis of a comparison of the integral 48 of the one or more isothermal regions (32a, 332a) and/or subregions of an adhesion with reference values of the respective integral 48. In relation hereto, FIG. 4 and FIG. 5 respectively show a thermographic representation corresponding to FIG. 2b and FIG. 3b, but with integral evaluation. The temperature distributions (440a, 442a) for the two measurement regions (40, 42) of a defect-free adhesion from FIG. 2a can again be seen in FIG. 4. As an example, FIG. 4 shows, in the region of the corrugation 25a, an integral 448a for a comparative temperature 442i, which serves to delimit the integration region. FIG. 5, on the other hand, shows the temperature distributions (540a, 542a) for the two measurement regions (340, 342) of a defective adhesion from FIG. 3a. As in FIG. 4, a comparative temperature 542i which serves to delimit the integration region is indicated in FIG. 5. As a result of the defect 35a (see FIG. 3a) in the region of the corrugation 25a of the measurement region 342, the temperature 96a and therefore also the integral 548a in the region of the corrugation 25a of the measurement region 342 is significantly smaller than an integral in a defect-free region (see integrals 448a and 548b). Alternatively or in addition, the evaluation may comprise the formation of a surface integral over a subregion of the thermographic data (30, 330, 430, 530) of one or more isothermal regions (32a, 332a) and/or subregions in the x direction 94 and the y direction 92. The adhesive quality can be judged here on the basis of a comparison of the surface integral of the one or more isothermal regions (32a, 332a) and/or subregions of an adhesion with reference values of the respective surface integral. The reference values for the comparison with the integral in the x direction 94 and/or the surface integral in the x direction 94 and the y direction 92 may comprise predetermined reference values here. Alternatively or in addition, the reference values can also be formed by taking an average of the previously checked adhesions. In particular, the reference values can be formed here by taking an average of the two previously checked adhesions, preferably of the five previously checked adhesions and particularly preferably of the at least ten previously checked adhesions. Alternatively, the reference value can also be manually input or amended by a machine operator. An adhesion can be judged as defect-free or the adhesive quality can be judged as sufficient here if the respective comparison shows a maximum deviation of 0% to 50%, preferably of 0% to 20% and particularly preferably of 0% to 5%.

The detection of the thermal radiation can also be carried out with an infrared camera 12 (see FIG. 1).

The computer program can also be configured to be implemented in-line during the process for producing paper adhesions, preferably corrugated cardboard adhesions.

The thermal radiation from one surface side of the first paper web 24 can also be detected, the normal vector thereof being aimed in the opposite direction of the at least second paper web (25, 26). Alternatively or in addition, the thermal radiation from one surface side of the at least second paper web (25, 26) can be detected, the normal vector thereof being aimed in the opposite direction of the first paper web 24.

In configurations of the method according to the invention, the paper adhesion may, in particular, be a corrugated cardboard adhesion.

In configurations of the method according to the invention, the product web may, in particular, be a corrugated cardboard web 28.

In configurations of the method according to the invention, the method can be carried out with a measurement system 1 according to any of the preceding embodiments.

I claim:

1. A measurement system adapted for use in a corrugating machine for processing corrugated cardboard, wherein the measurement system comprises a measurement device;
   wherein;
   the measurement device detects electromagnetic waves in the infrared range and is aimed at a region of a transportation device of the corrugating machine in the direction of transportation downstream of an adhesion station of the corrugating machine,
and further wherein the measurement device comprises an evaluation device for evaluating the detected electromagnetic waves in the infrared range, the evaluation device comprises a computer with a memory device, wherein a computer program for checking the process of producing adhesions of a first paper web to at least a second paper web to form a product web that is stored on the memory device, the computer program being configured to carry out the following steps:
   Detecting thermal radiation of the product web after adhesion of the first paper web to the at least second paper web;
   Producing thermographic data based on the thermal radiation;
   Evaluating the thermographic data; and
   Judging the adhesive quality of the paper adhesion on the basis of the evaluation, and further, wherein the evaluation comprises a spatially resolved determination of the geometric dimensions, of the length in the x direction and/or of the width in the y direction, of one or more isothermal regions and/or subregions in the thermographic data.

2. The measurement system according to claim 1, wherein the measurement device is configured to detect the temperature.

3. The measurement system according to claim 2, wherein the measurement device is configured to thermographically display and analyze a detected temperature distribution.

4. The measurement system according to claim 1, wherein the measurement device comprises an infrared camera.

5. The measurement system according to claim 1, wherein the measurement device is configured to detect a temperature distribution of the corrugated cardboard along the width of the web.

6. The measurement system according to claim 1, wherein the thermal radiation of the product web is detected in a detection region which extends linearly in the y direction of the product web and/or two-dimensionally in the x and y directions of the product web.

7. The measurement system according to claim 1, wherein the adhesive quality is judged on the basis of a geometrical evaluation of the thermographic data.

8. The measurement system according to claim 1, wherein the evaluation comprises the formation of an integral and/or surface integral over a linear subregion of the thermographic data of one or more isothermal regions and/or subregions in the x direction.

9. The measurement system according to claim 8, wherein the adhesive quality is judged on the basis of a comparison of the geometric dimensions and/or of a comparison of the integral and/or of a comparison of the surface integral of the one or more isothermal regions and/or subregions of an adhesion with reference values of the geometric dimensions.

10. The measurement system according to claim 9, wherein the reference values comprise predetermined reference values and/or are formed by taking an average of the previously checked adhesions.

11. The measurement system according to claim 8, wherein the adhesive quality is judged on the basis of a comparison of the geometric dimensions and/or of a comparison of the integral and/or of a comparison of the surface integral of the one or more isothermal regions and/or subregions of an adhesion with reference values of the geometric dimensions.

12. A corrugating machine comprising: a transportation device for transporting corrugated cardboard in a transport direction, an adhesion station configured to adhere a first paper web to at least a second paper web, and a measurement system for checking the process of producing adhesions of the corrugated cardboard; wherein the measurement system is a measurement system according to claim 1.

13. A method of evaluating a process for producing adhesions of a first paper web to at least a second paper web to form a product web, using a measurement system, characterized by the steps of:
  Detecting thermal radiation of the product web after adhesion of the first paper web to the at least second paper web;
  Producing thermographic data based on the thermal radiation;
  Evaluating the thermographic data, wherein the evaluation comprises a spatially resolved determination of the geometric dimensions of the length in the x direction and/or of the width in the y direction, of one or more isothermal regions and/or subregions in the thermographic data; and
  Judging the adhesive quality of the paper adhesion on the basis of the evaluation.

14. The method according to claim 13, wherein the thermal radiation from one surface side of the respective first and/or the at least second paper web is detected, the normal vector thereof being aimed in the opposite direction of the respective other paper web.

15. The method according to claim 13, wherein the method is carried out with a measurement system wherein; the measurement device detects electromagnetic waves in the infrared range and is aimed at a region of a transportation device of the corrugating machine in the direction of transportation downstream of an adhesion station of the corrugating machine.

* * * * *